(12) United States Patent
Hochschuler et al.

(10) Patent No.: US 8,936,627 B2
(45) Date of Patent: Jan. 20, 2015

(54) EXPANDABLE SPINAL SUPPORT DEVICE WITH ATTACHABLE MEMBERS AND METHODS OF USE

(75) Inventors: Stephen H. Hochschuler, Paradise Valley, AZ (US); Skott E. Greenhalgh, Lower Gwynedd, PA (US); John Paul Romano, Chalfont, PA (US); Robert A. Kiefer, Quakertown, PA (US); Wade Kevin Trexler, Coopersburg, PA (US); Michael P. Igoe, Perkasie, PA (US)

(73) Assignee: Alphatec Spine, Inc., Carlsbad, CA (US)

( * ) Notice: Subject to any disclaimer, the term of this patent is extended or adjusted under 35 U.S.C. 154(b) by 402 days.

(21) Appl. No.: 12/755,271

(22) Filed: Apr. 6, 2010

(65) Prior Publication Data

US 2010/0217325 A1    Aug. 26, 2010

Related U.S. Application Data

(63) Continuation-in-part of application No. 12/264,181, filed on Nov. 3, 2008, and a continuation-in-part of application No. 12/255,820, filed on Oct. 22, 2008, now Pat. No. 7,961,030.

(60) Provisional application No. 61/167,120, filed on Apr. 6, 2009.

(51) Int. Cl.
  *A61B 17/86*     (2006.01)
  *H03K 17/28*     (2006.01)
  *A61B 17/70*     (2006.01)
  *H03K 17/22*     (2006.01)

(52) U.S. Cl.
  CPC ............. *A61B 17/864* (2013.01); *H03K 17/28* (2013.01); *A61B 17/7098* (2013.01); *A61B 2017/8655* (2013.01); *H03K 17/223* (2013.01); *A61B 17/7058* (2013.01); *A61B 17/8625* (2013.01); *A61B 17/7037* (2013.01)
  USPC ............ 606/301; 606/300; 606/310; 606/313

(58) Field of Classification Search
  USPC ................... 623/17.11–17.16; 606/300, 301, 606/305–308, 313
  See application file for complete search history.

(56) References Cited

U.S. PATENT DOCUMENTS

| | | | |
|---|---|---|---|
| 5,059,193 A | | 10/1991 | Kuslich |
| 5,167,664 A | * | 12/1992 | Hodorek ....................... 606/306 |
| 5,571,189 A | | 11/1996 | Kuslich |
| 6,974,460 B2 | | 12/2005 | Carbone |
| 7,922,748 B2 | * | 4/2011 | Hoffman ....................... 606/267 |
| 2004/0015172 A1 | * | 1/2004 | Biedermann et al. ........... 606/73 |
| 2004/0122431 A1 | | 6/2004 | Biedermann |
| 2005/0251140 A1 | | 11/2005 | Shaolian |
| 2007/0093899 A1 | * | 4/2007 | Dutoit et al. ............... 623/17.11 |

(Continued)

*Primary Examiner* — Nicholas Woodall
(74) *Attorney, Agent, or Firm* — Michael J. Loi

(57) ABSTRACT

Expandable support devices for tissue repair are disclosed. The devices can be used to repair hard or soft tissue, such as bone or vertebral discs. A method of repairing tissue is also disclosed. Surgical devices and methods for adjusting (e.g., removing, repositioning, resizing) deployed orthopedic expandable support devices are also disclosed. The expandable support devices can be engaged and surgically implanted by an engagement device and affixed to bone to provide stability and support for the devices. The expandable support devices are attachable to spinal fixation devices such as screws or plates, and may be used to support such devices when placed in weakened or damaged areas of bone.

13 Claims, 12 Drawing Sheets

(56) References Cited

U.S. PATENT DOCUMENTS

2007/0168043 A1 7/2007 Ferree
2008/0288003 A1* 11/2008 McKinley ..................... 606/313
2009/0125028 A1* 5/2009 Teisen et al. ..................... 606/63

* cited by examiner

NOT INVENTION

NOT INVENTION

NOT INVENTION

NOT INVENTION

EXPANDABLE SPINAL SUPPORT DEVICE WITH ATTACHABLE MEMBERS AND METHODS OF USE

CROSS-REFERENCE TO RELATED APPLICATIONS

This application claims priority to U.S. Provisional Application No. 61/167,120, filed Apr. 6, 2009, which is incorporated by reference herein in its entirety.

This application is a continuation-in-part of U.S. patent application Ser. No. 12/255,820, filed Sep. 10, 2009, which is incorporated by reference herein in its entirety.

This application is also a continuation-in-part of U.S. patent application Ser. No. 12/264,181, filed Nov. 3, 2008, which is incorporated by reference herein in its entirety.

BACKGROUND OF THE INVENTION

1. Field of the Invention

Embodiments of the present application relate to a device and method for attaching to bones, for example to repair spinal compression fractures and to provide fixation to adjacent vertebra, and methods of using the same.

2. Description of the Related Art

Broken bones, such as compression fractures of one or more vertebrae in the spine, may be treated with internal fixation. Any indication needed spinal stability can also be treated by internal fixation. Examples include scoliosis, kyphosis, spondylothisthesis and rotation, segmental instability, such as disc degeneration and fracture caused by disease and trauma and congenital defects, and degeneration caused by tumors.

As shown by FIG. 1, internal fixation in the spine is often accomplished by first screwing fixation screws into the pedicles and vertebral bodies of the vertebrae 10. FIG. 2 shows that the fixation screws are then typically attached to a rigid fixation rod or plate that provide support between one or more weakened vertebra 10. This support often immobilizes the vertebra 10 to which the fixation screws have been inserted.

FIG. 3 illustrates that existing fixation systems often have the fixation rod 14 or plate, through which a number of fixation screws 12 are deployed. The screw head 18 prevents the fixation rod 14 from separating from the fixation screw 12. The fixation screw 12 also has a screw body 16 which has a screw longitudinal axis 20 often static relative to the fixation rod 14.

FIG. 4 illustrates that in some existing fixation systems, the fixation screws 12 can be polyaxial screws attached to the fixation rod 14 or plate in a manner so that the screw longitudinal axis 20 can rotate, as shown by arrows, with respect to the fixation rod 14.

Many patients are not candidates for existing fixation systems described above due to compression fractures in the vertebra. In these cases, if the screw is placed in the fracture, the bones can fail and the fixation screws 12 can be ripped from the bone resulting in complete failure and additional damage to the bone.

Vertebroplasty is often used to treat compression fractures in the vertebra, such as those caused by osteoporosis, cancer, or stress. Vertebroplasty is an image-guided, minimally invasive, nonsurgical therapy for injecting an orthopedic cement mixture through a needle into the fractured bone. The mixture fills or substantially fills the cavity of the compression fracture and is limited to certain chemical compositions, thereby limiting the amount of otherwise beneficial compounds that can be added to the fracture zone to improve healing. In an alternative procedure known as kyphoplasty, a balloon is first inserted in the compression fracture and the vertebra is expanded before the cement is injected into the newly formed space.

It would be desirable to provide a fixation screw can provide a higher anchoring force in vertebra having compression fractures, minimize bone failure and substantially eliminate the risk of backout.

SUMMARY OF THE INVENTION

Certain embodiments of the present disclosure provide for systems and methods that can be used to repair hard or soft tissue, such as bone or vertebral discs. In one embodiment, expandable support devices for tissue repair are disclosed. Surgical devices and methods for adjusting (e.g., removing, repositioning, resizing) deployed orthopedic expandable support devices are also disclosed. The expandable support devices can be engaged and surgically implanted by an engagement device and affixed to bone to provide stability and support for the devices.

In one embodiment, the expandable support devices are attachable to other spinal fixation devices, and may be used to support such devices when placed in weakened or damaged areas of bone. For example, an expandable support device may be placed in a damaged vertebral body to support the vertebral body. The expandable support device may be further secured in bone using a filler such as bone cement. A spinal fixation device such as a pedicle screw or plate may be attached to the expandable support device, with the expandable support device providing a desired support and location for hold the fixation device in place.

In one embodiment, a vertebral support system comprises an expandable support device comprising a proximal end portion, a distal end portion, and a longitudinal axis extending there between. The expandable support device is configured for delivery within or between spinal vertebral bodies. A spinal fixation device is attached to one of the end portions.

In another embodiment, a method for repairing a damaged section of a spine is provided. An expandable support device having a proximal end and a distal end is delivered into the damaged section. The expandable support device is expanded in the damaged section to support the damaged section. A spinal fixation device is attached to the proximal end of the expandable support device.

DETAILED DESCRIPTION OF THE PREFERRED EMBODIMENTS

Figure 1:
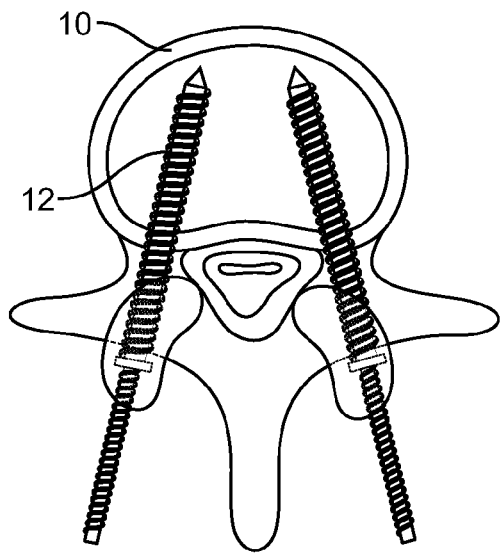
FIG. 1 is a partially see-through top view of a vertebra with fixation screws therethrough.
Figure 2:
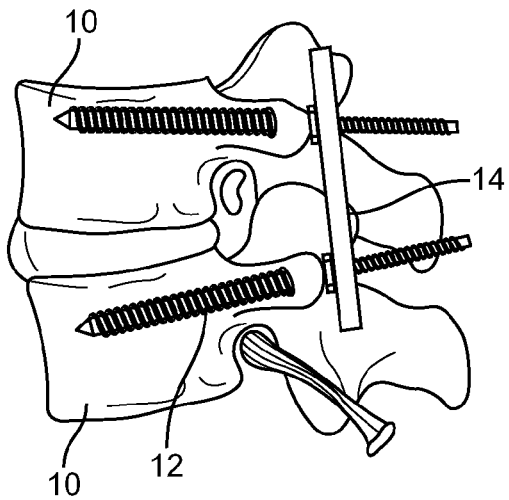
FIG. 2 is a partially see-through lateral view of a section of the spine with fixation screws and a fixation rod.
Figure 3:
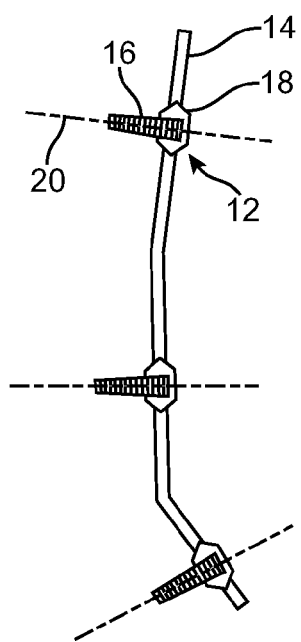
FIGS. 3 and 4 illustrate simplified variations of existing fixation systems.
Figure 4:
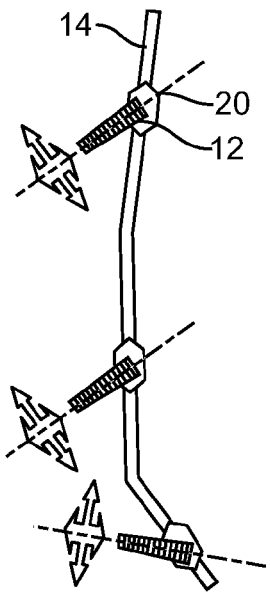
Figure 5:
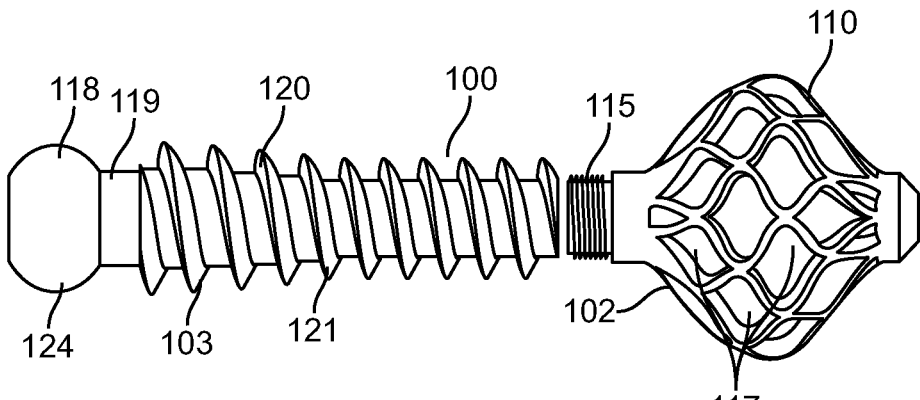
FIG. 5 shows an exploded view of one embodiment of an spinal fixation device.
Figure 6:
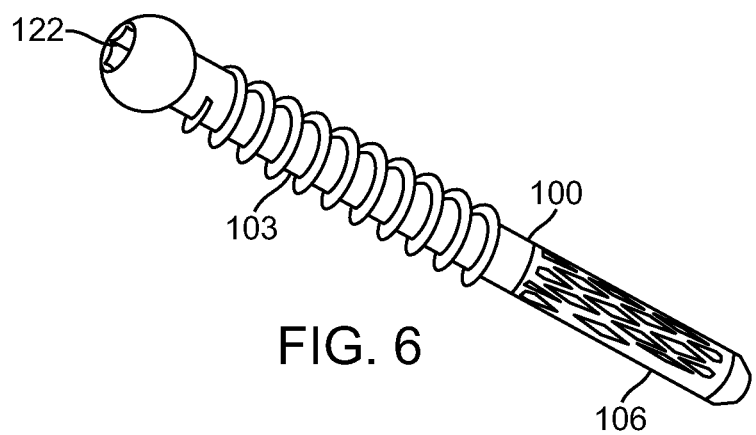
FIG. 6 shows the assembled spinal fixation device with the expandable support device in the contracted position.
Figure 7:
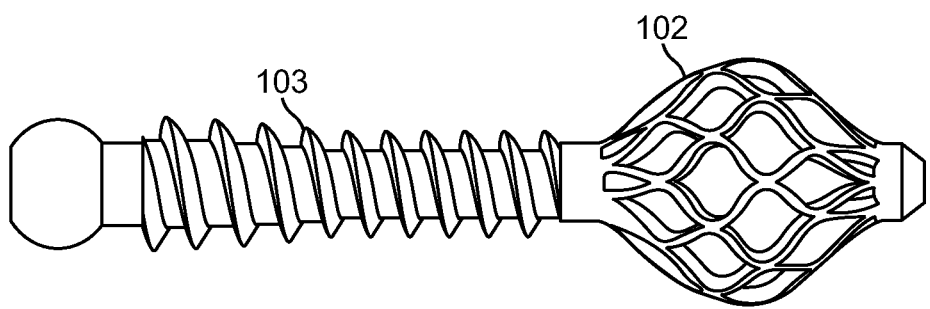
FIG. 7 shows the assembled spinal fixation device with the expandable support device in the expanded condition.

FIGS. 5-7 illustrate one embodiment of a spinal fixation device 100 consisting of a biocompatible expandable support device or implant 102 coupled with an attachable member 103 to form the spinal fixation device 100. In one particularly preferred embodiment, the attachable member 103 includes a body portion (see FIGS. 8 and 9) forming a polyaxial pedicle screw which is fixedly attachable to the expandable support device 102 via screw thread engagement elements 115 on the radial outside of expandable support device 102 and corresponding screw thread engagement elements on the radial inside of polyaxial pedicle screw 103 (not shown). FIG. 5 illustrates an expanded support device 102 and polyaxial screw 103 before they are physically attached together, while FIGS. 6 and 7 show a pre-expanded support device 102 attached to polyaxial screw 103 and an expanded support device 102 attached to a polyaxial screw 103, respectively. Suitable screws that may be modified to include an attachment mechanism for attaching to the expandable support device 102 include Zodiac® polyaxial screws available from Alphatec Spine. Other suitable screws include those described in U.S. Publication No. 2008/0243189 and U.S. Pat. No. 7,377,923, the entirety of each of which is hereby incorporated by reference.

With reference to FIG. 5, the polyaxial screw 103 comprises a head portion 118, a neck portion 119, and a shaft portion 120. In some embodiments (not shown), the polyaxial screw further includes other components such as those described in U.S. Publication No. 2008/0243189 and U.S. Pat. No. 7,377,923 referenced above. In one particular embodiment, the polyaxial screw comprises a substantially spherical head portion, a threaded shaft portion and a tool engagement recess defined by the head portion for use in driving the pedicle screw into vertebrae. The polyaxial screw also comprises a body member for receiving a head portion of the pedicle screw which defines an opening in an inner end thereof for the extension of the shaft portion of the screw there through, see FIGS. 8 and 9. The body member has a pair of opposed parallel slots for receiving a portion of a fixation rod there between. The body member also has a curvilinear interior surface disposed about the opening for abutting and mating with the substantially spherical head portion of the screw so as to allow variable angular movement of the body member with respect to the pedicle screw while maintaining the interior surface of the body member in mating contact with the head portion of the screw. The polyaxial screw further comprises a locking cap releasably securable within the body member such that the cap bears against the portion of a fixation rod disposed between the slots to secure the rod within the assembly. The polyaxial screw also comprises a keyed interface between the pedicle screw and the body member whereby the pedicle screw can be inserted into a vertebrae and the body member subsequently disposed about the substantially spherical head portion of the screw such that the head portion abuts and mates with the curvilinear interior surface of the body member to provide the variable angular movement of the body member with respect to the screw. The keyed interface comprises a first threaded surface in the body member about the opening in the inner end thereof and a second threaded surface on the head portion of the screw. The first threaded surface is adapted to threadably engage the second threaded surface such that the screw can be inserted into a vertebrae and the body member can be threaded onto and over the head portion of the screw to position the curvilinear interior surface of the body member such that the interior surface can abut and mate with the body portion.

In other embodiments, the shaft portion 120 can have a tapered shape with a screw thread 121 about the radial outside of shaft portion 120. In other embodiments, the shaft portion 120 can have a non-tapered shaped and/or no radial outside screw threads 121. In one particular embodiment, polyaxial screw 103 can have hollow shaft 120, neck 119 and head 118 portions along the inner longitudinal axis of the polyaxial screw in order to allow a guide wire (not shown) to be threaded through the polyaxial screw to help facilitate insertion of the screw during surgery. Additionally, the radial inside of polyaxial screw 103 at its distal end can have screw threading (not shown) to allow it to fixedly and releasably attach to expandable support device 102. It shall be understood that a variety of shaft designs are interchangeable with the present design. The specific choice of shaft features, such as thread pitch, shaft diameter to thread diameter ratio, overall shaft shape, etc. may be varied as needed.

The head portion 118 of the screw 103 can comprise a semi-spherical shape, which has a recess 122 in it (see FIG. 6, discussed in further detail below). It is to be understood that the semi-spherical shape can be a section of a sphere, greater in extent than a hemisphere, and exhibiting an external contour which is equidistant from a center point of the head. In a preferred embodiment, the major cross-section of the semi-spherical head portion 118 includes at least 270 degrees of a circle.

Referring to FIG. 6, the recess 122 of screw 103 defines a receiving locus for the application of a torque for driving the screw 103 into bone. The specific shape of the recess 122 may be chosen to cooperate with any suitable screw driving tool. For example, the recess 122 may comprise a slot for a flat-head screwdriver, a crossed recess for a Phillips head screwdriver, or most preferably, a hexagonally shaped hole for receiving an Allen wrench. It is further preferable that the recess 122 be co-axial with the general elongate axis of the screw 103, and most particularly with respect to the shaft portion 120. Having the axes of the recess 122 and the shaft portion 120 co-linear facilitates the step of inserting the screw 103 into bone in some embodiments.

Referring back to FIG. 5, the expandable support device 102 can have one or more ingrowth ports 117. The ingrowth ports 117 can be formed by the open spaces between one or more adjacent struts 110. The ingrowth ports 117 can be configured to encourage biological tissue ingrowth there through during use. The ingrowth ports can be configured to increase, and/or decrease, and/or focus pressure against the surrounding biological tissue during use. The ingrowth ports can be configured to increase and/or decrease the stiffness of the support struts 110.

The expandable support device 102 can also have one or more protrusions on the surface of the expandable support device 102 (not shown). The protrusions can have features such as tissue hooks, and/or barbs, and/or cleats. The protrusions can be integral with and/or fixedly or removably attached to the expandable support device 102. The expandable support device 102 can be configured (e.g., on the support struts 110 or other parts of the implant) to burrow into soft bone (e.g., cancellous or diseased), for example, until the device fully expands, or until the device hits the harder vertebral endplates.

Figure 8:
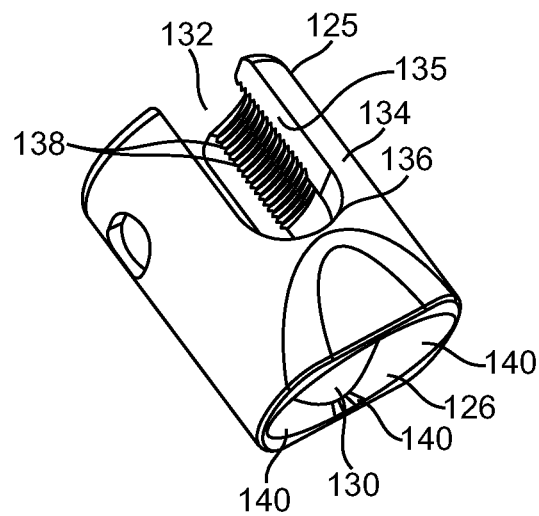
FIG. 8 shows a perspective view of the body member.
Figure 9:
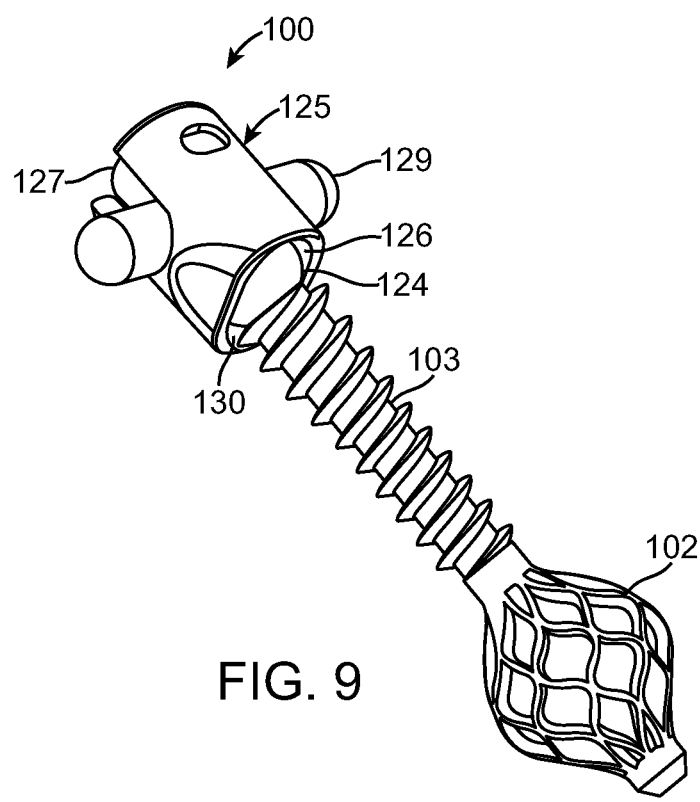
FIG. 9 is a perspective view of the variable angle spinal screw assembly of the present invention.

FIGS. 8 and 9 show the spinal fixation device 100 including the screw 103, body member 125 and locking cap 127. The spinal fixation device 100 is used with at least one other such device and a stabilization or fixation rod 129 to connect the assemblies and stabilize the vertebras into which the assemblies are inserted. As discussed above, the screw 103 has a spherical head 118 defining slot 122 therein used to drive the screw into the bone. The rounded surface defined by the lower portion of screw head 118 rests upon and mates with a rounded interior surface 126 formed in the inner or lower end of the body member 125 so as to form a modified ball joint that provides the desired variable angular movement of the body member with respect to the embedded pedicle screw. The threaded shaft portion of screw 103 extends therefrom through the opening 130 in the lower end of body member 125.

The body member 125 further defines a pair of opposed parallel slots 132 axially disposed in the side wall 134 thereof, which terminate at their lower ends in curvilinear surfaces 136. The two slots 132 are sized to receive the fixation rod 129 therein as shown in the drawings with the walls 135 defining the slots preferably extending upwardly beyond the midpoint of the rod and can be inclined slightly to provide a slight holding force on the rod prior to securing the rod with the locking cap 127. Thus, during assembly, the surgeon exerts a slight downward force on the rod, snapping the rod into the transverse channel defined by the aligned slots 132.

The outer or upper interior surface of side walls 134 of the body member 125 both have radially projecting serrations formed therein defining a plurality of axially aligned ratchet teeth or threads 138 that mate with external threads on the locking cap 127. The exterior bottom surface of body member 125 has spaced outwardly extending concave surface 140 formed therein and a pair of perpendicularly disposed concave surfaces 142. Surfaces 140 and 142, together with mating surfaces 124 and 126 on the screw head and body member of the assembly, provide an extended range of motion of the body member 125 with respect to the screw 103. In one embodiment, the range of motion is about +/−30° in all directions (as measured from the longitudinal axis of the screw) and about +/−40° in the inferior-superior direction, the outwardly (as viewed from the screw head) concave surfaces provide the +/−40° range of motion, for a total motion range of 80°. This extended range of motion, as compared to the prior art, allows the surgeon additional freedom in locating the screws and eases the assembly process by reducing the requirement for a rod contouring.

Figure 10:
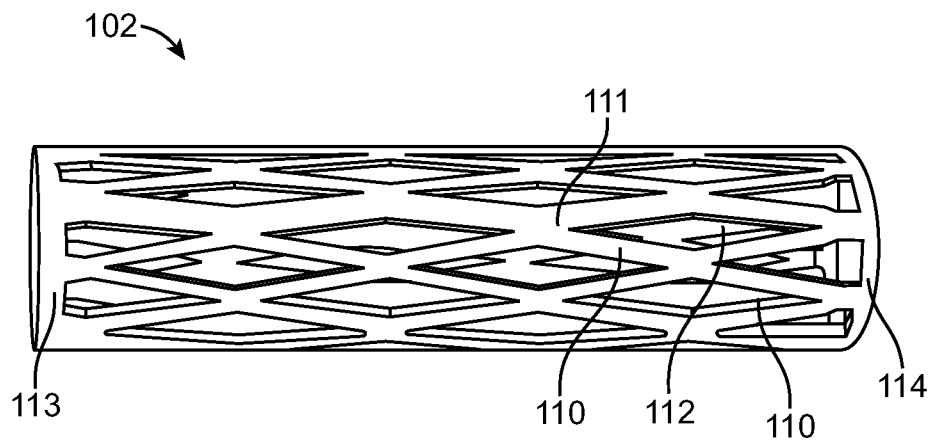
FIG. 10 illustrates a variation of the expandable section in a radially contracted configuration.

FIG. 10 illustrates that the expandable support device 102 can have a number of struts 110 attached to each other at joints 111. When the expandable support device 102 is in a radially contracted configuration, the struts 110 can be configured to form diamond-shaped ports 112. The expandable section 102 can have a near or proximal end portion 113 and a far or distal end portion 114. The struts 110 can attach to proximal and distal ends 113, 114.

Figure 11:
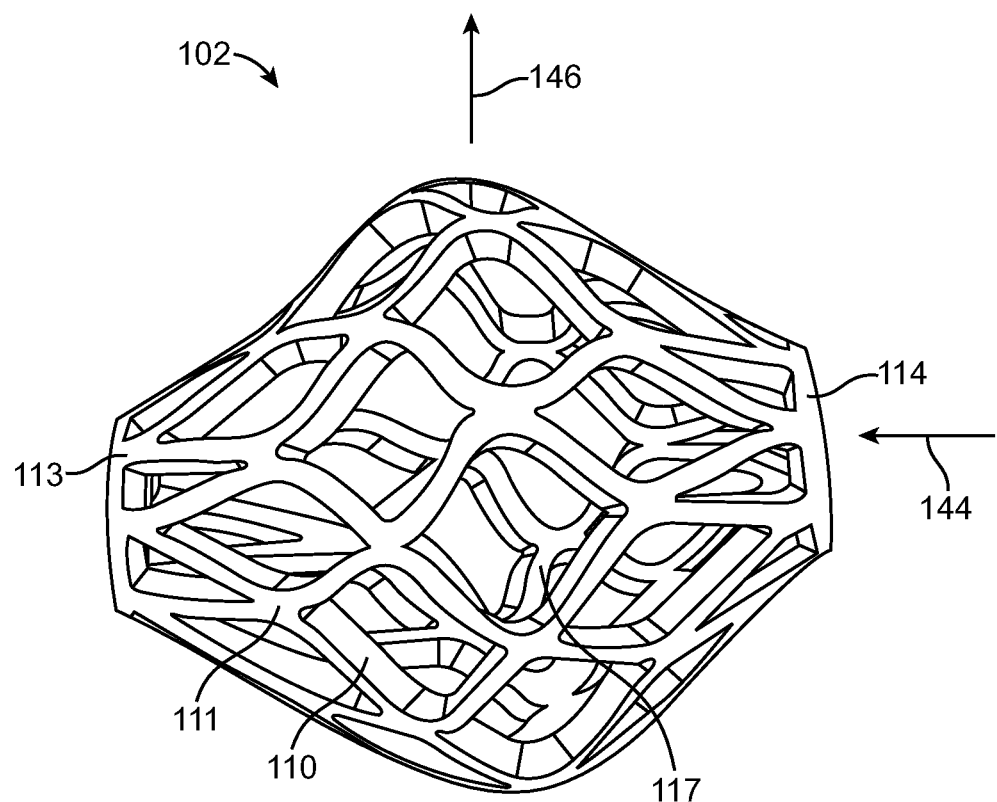
FIG. 11 illustrates the expandable section of FIG. 10 in a radially expanded configuration.

FIG. 11 illustrates that longitudinal compressive force 144 can be applied to the expandable section, for example resulting in radial expansion 146. In a radially expanded configuration, the struts can deform near the joints and the diamond-shaped ports 112 expand into ingrowth ports 117. The proximal and distal ends 113, 114 can remain substantially static.

Figure 12A:
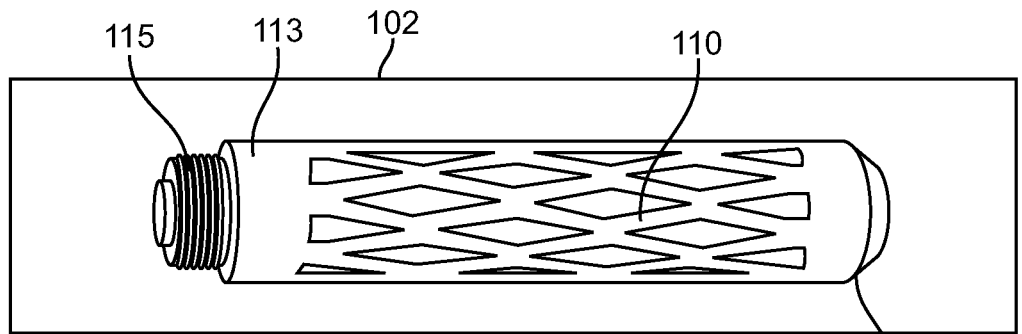
FIGS. 12A-12C illustrates side views of additional embodiments of the expandable support device having various sizes in their unexpanded configurations.
Figure 12B:
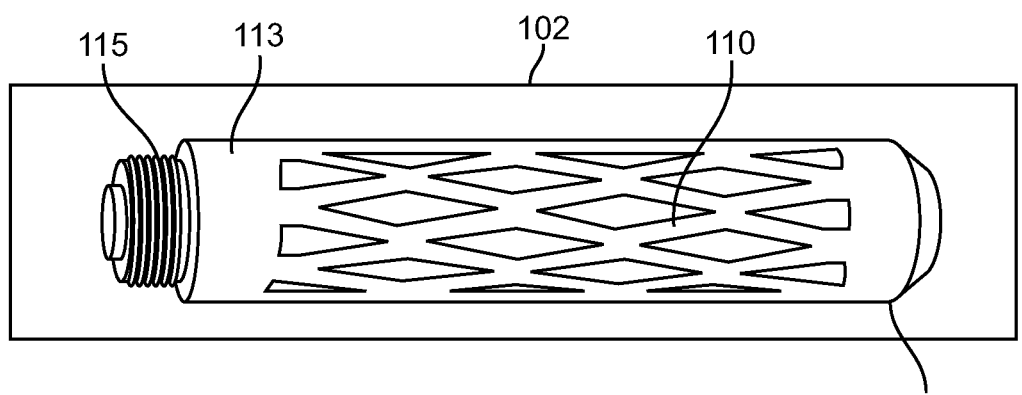
Figure 12C:
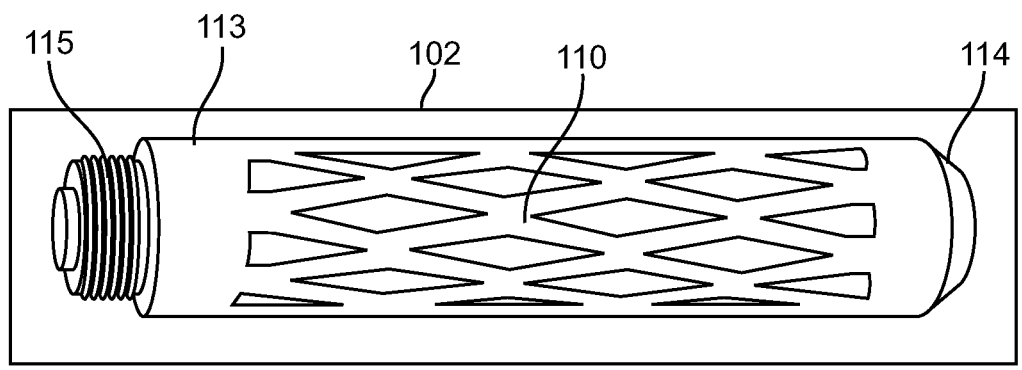

FIGS. 12A-12C illustrate embodiments of biocompatible expandable support devices 102 of varying sizes used for tissue repair, including, but not limited to repair of bone fractures such as spinal compression fractures, and/or repairing soft tissue damage, such as herniated/diseased vertebral discs. The expandable support devices 102 can be used to perform vertebroplasty, partial or complete vertebra or vertebral disc replacement, vertebral fixation or combinations thereof. The implant can be an expandable support device 102, for example a stent.

The expandable support devices 102 can be used to provide structural reinforcement from inside one or more bones, as a replacement for one or more bones, or between bones. The expandable support devices can be used for a variety of orthopedic locations, such as in the vertebral column, for example, to treat compression fractures. Examples of expandable support devices and methods suitable for use as expandable support devices 102, as well as devices for deploying the expandable support devices include those disclosed in the following applications which are all incorporated herein in their entireties: PCT Application Nos. US2005/034115, filed 21 Sep. 2005; US2005/034742, filed 26 Sep. 2005; US2005/034728, filed 26 Sep. 2005; US2005/037126, filed 12 Oct. 2005; US2006/016553, filed Apr. 27, 2006; US2006/016554, filed Apr. 27, 2006; US2006/027601, filed Jul. 14, 2006; US2006/038920, filed Apr. 10, 2006; US2007/131002, filed May 1, 2007; and US2008/003421, filed Mar. 18, 2008; and U.S. patent application Ser. No. 11/457,772, filed Jul. 14, 2006; Ser. No. 12/264,181, filed Nov. 3, 2008; and Ser. No. 12/456,602, filed Jun. 18, 2009.

Figure 13:
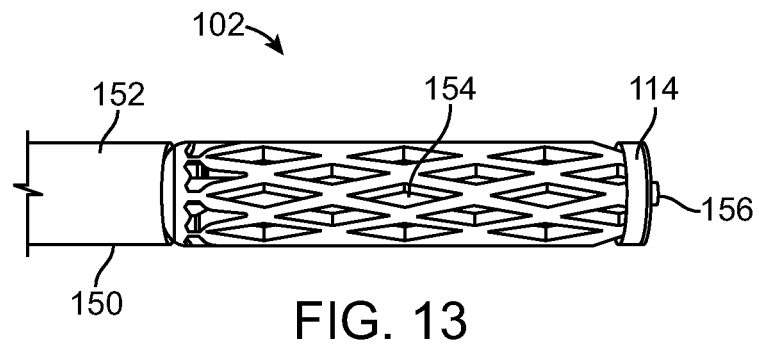
FIG. 13 illustrates a variation of the expandable section in a radially contracted configuration on the expandable attachment device.
Figure 14:
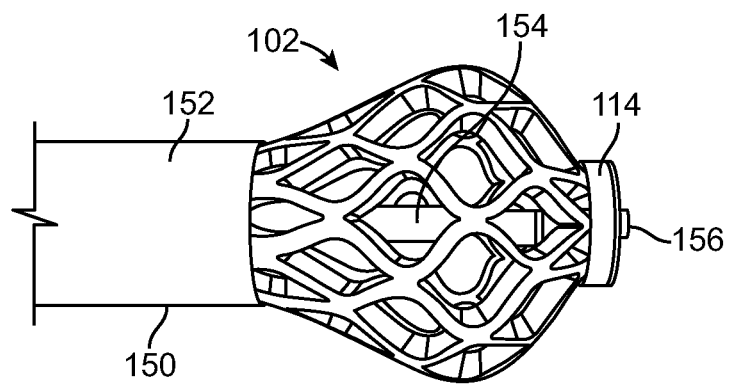
FIG. 14 illustrates a variation of the expandable section in a radially expanded configuration on the expandable attachment device.

FIGS. 13 and 14 illustrates that the expandable support device 102 can be radially expanded by longitudinally compressing the expandable section. For example, a deployment tool 150 can have a portion 152 that attaches to the threads at the proximal 113. The expandable support device 102 can be compressed between the deployment tool 150 and the distal end 114.

The deployment tool 150 can have a deployment rod 154, for example to transmit the compressive force to the distal end 114. The deployment rod 154 can be releasably attached 156 to a threaded portion 116 at the distal end 114 (see FIG. 15). The deployment rod 154 can be released and removed after the expandable section is radially expanded.

In the embodiments shown in FIGS. 5-14, the expandable support devices 102 have a plurality of struts 110 connecting a near or proximal end portion 113 and a far or distal end portion 114. The struts 110 can be arranged in a crisscross pattern forming open spaces having a substantially diamond-like shape 112 that can deform as the implant expands to form ingrowth ports 117. The expandable support devices 102 can be constructed of separate structures that are fixed, integrated, or otherwise joined together. Alternatively, the expandable support device 102 can be fabricated from a uniform stock of material (e.g., via laser cutting or electrical discharge machining (EDM)). The expandable support device 102 can be constructed of separate structures that are fixed, integrated or otherwise joined together. The struts 110 are deformable and can have a thinner cross sectional thickness than most of the remainder of the stent to allow for pre-determined deformation of the expandable support devices 102 to take place. In the pre-expanded configuration, the cross-sectional shape of the expandable support devices 102 can be substantially circular and uniform, triangular, oval, rectangular, square, or any type of polygon and/or rounded, and/or tapered shape. In the pre-expanded configuration, the diamond-shaped ports 112 may be approximately the same size or may be different sizes that expand differently. Upon expansion, the expandable support device 102 can form a polygon-type shape, or other shape as discussed herein. Upon expansion, the ingrowth ports 117 may be approximately the same size or may be different sizes.

In some embodiments, at least one of the near and far end portions 113 and 114 of the expandable support devices 102 can have one or more engagement elements 115 to receive an attachable member such as a spinal fixation device (discussed in further detail below). The engagement elements 115 can be on the radial inside and/or radial outside of the near or far end portions 113 and 114. The engagement elements 115 can be a screw thread, a keyed slot, a toggle, ball and socket, an interference fit, a clip, a ratchet, a magnet, glue, an expanding anchor clip, an abutment, a hook, or combinations thereof. In the embodiment shown, the expandable support devices 102 have screw thread engagement elements 115 on the radial outside of the near end portion 113 configured to receive a threaded attachable member.

Similar to previously discussed devices, the expandable support devices 102 can be made from, for example, a single or multiple stainless steel alloys, nickel titanium alloys (e.g., Nitinol), surgical grade titanium alloy (for example, Ti-6AI-4V, ASTM F 136), commercially pure titanium (for example, Ti-CP2, ASTM F 67) with or without an electrolytic conversion coating, cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N. V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA)$_5$ polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

Figure 15:
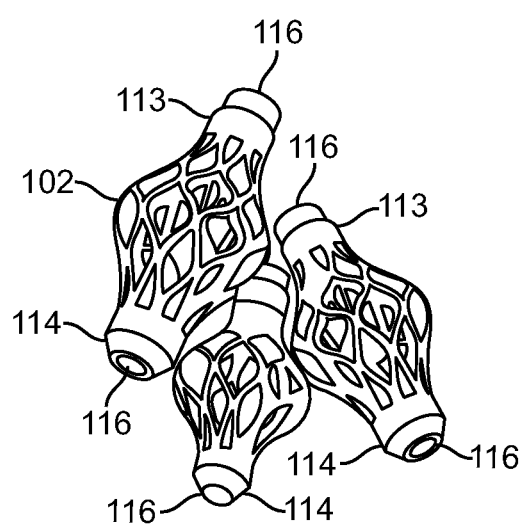
FIG. 15 shows perspective views of the implants of FIGS. 12A-12C in expanded configurations.

With reference to FIG. 15, the expandable support devices 102 can be expanded to obtain a non-uniform circular cross-sectional shape with increasing cross-sectional diameter toward the middle of the expandable support devices 102 and decreasing cross-sectional diameter toward the near end portions 113 and far end portions 114 of the expandable support devices 102.

The expansion ratio of the expandable support devices 102 can be, for example, about 2 to 4 times the initial diameter of the expandable support devices 102. The expansion ratio can be selected as required for the particular procedure. For example, in the pre-expanded configuration the expandable support device 102 of FIG. 12A can have an initial diameter of about 4.5 mm, while in the expanded configuration, the diameter can be about 11.4 mm. In a further example, the expandable support device 102 of FIG. 12B can have an initial diameter of about 5.5 mm, while in the expanded configuration, the diameter can be about 13 mm. In yet another example, the expandable support device 102 of FIG. 12C can have an initial diameter of about 7.0 mm, while in the expanded configuration, the diameter can be about 14.8 mm. However, one of skill in the art will understand that the expandable support devices disclosed herein can any number of sizes without departing from the spirit or scope of the invention.

The end portions of the expandable support device 102 can have openings 116. In one preferred embodiment, the openings 116 are threaded to accommodate a threaded attachable member. One or both of the end portions can be solid which allows for filling of the expandable support device 102 with materials described herein. The end portions can be expandable or non-expandable (i.e., rigid).

The expandable support device 102 and/or attachable member 103 can be completely or partially coated with agents and/or a matrix for cell ingrowth or used with a fabric, for example a covering (not shown) that acts as a matrix for cell ingrowth. The matrix and/or fabric can be, for example, polyester (e.g., DACRON® from E. I. Du Pont de Nemours and Company, Wilmington, Del.), polypropylene, PTFE, ePTFE, nylon, extruded collagen, silicone or combinations thereof.

The expandable support devices 102 and/or threaded member 103 and/or the fabric can be filled, coated, layered and/or otherwise made with and/or from cements, fillers, glues, and/or an agent delivery matrix known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rhBMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatory drugs (NSAIDs) such as cyclooxygenase-1 (COX-I) inhibitors (e.g., acetylsalicylic acid, for example ASPIRIN® from Bayer $AG_5$ Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-I inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostaglandin $E_2$ Synthesis in Abdominal Aortic Aneurysms, Circulation, Jul. 6, 1999, 48-54; Tambiah et al, Provocation of Experimental Aortic Inflammation Mediators and Chlamydia Pneumoniae, Brit. J. Surgery 88 (7), 935-940; Franklin et al, Uptake of Tetracycline by Aortic Aneurysm Wall and Its Effect on Inflammation and Proteolysis, Brit. J. Surgery 86 (6), 771-775; Xu et al, SpI Increases Expression of Cyclooxygenase-2 in Hypoxic Vascular Endothelium, J. Biological Chemistry 275 (32) 24583-24589; and Pyo et al, Targeted Gene Disruption of Matrix Metalloproteinase-9 (Gelatinase B) Suppresses Development of Experimental Abdominal Aortic Aneurysms, J. Clinical Investigation 105 (11), 1641-1649 which are all incorporated by reference in their entireties.

Figure 16:
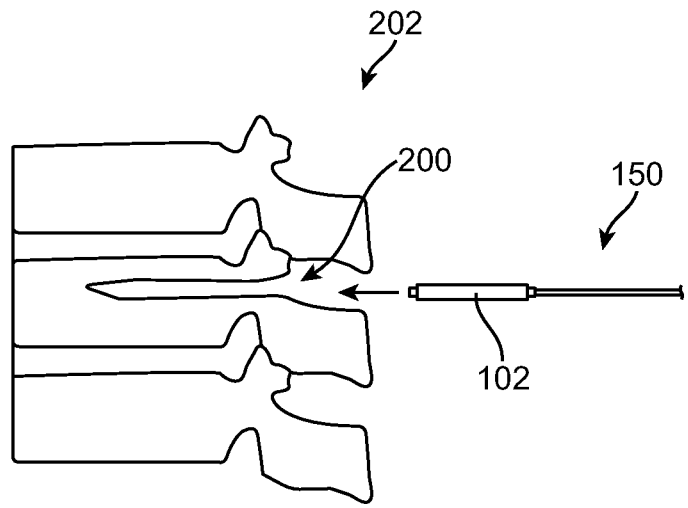
FIGS. 16 and 17 illustrate a variation of a method for deploying the expandable support device into the treatment site in the vertebra.
Figure 17:
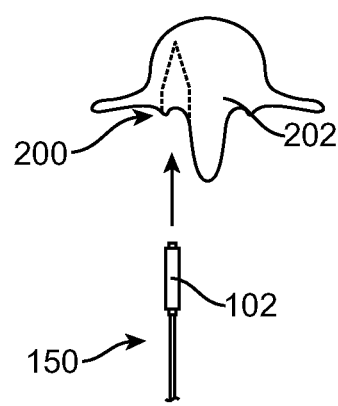

FIGS. 16 and 17 illustrate that the expandable support device 102 can be coupled to the deployment tool 150 and inserted into a prepared hole within the spine. The deployment tool 150 can be deployed from the posterior side of the vertebral column 202. The deployment tool 150 can be deployed off-center, for example, when approaching the posterior side of the vertebral column 202. Once inserted, the expandable support device 102 can be deployed and/or expanded with a force from a mechanical actuation device. For example, the ends of the expandable support device 102 can move, or be moved, together to expand the backbone struts outward. In some embodiments, the expandable support device 102 can be configured to be self-expand upon the removal of a restraint (e.g., when the expandable support device 102 is constructed from a resilient or super-elastic material). The expandable support device 102 can be made from a shape memory alloy that can have a pre-determined transition temperature such that expansion takes place due to temperature changes passively (e.g., from the patient's body heat) or actively (e.g., from thermal and/or electrical energy delivered to the expandable support device 102 from outside the patient) created during or after implantation.

The expandable support device 102 can be locked into the expanded configured with a locking structure (e.g., a center strut, ratchet type mechanism, screw, locking arm, combinations thereof) that can be integral with or separate from the remainder of the expandable support device 102. The expandable support device 102 can be "locked" into the expanded position by filing the expandable support device 102 with cement, filler (bone chips), calcium sulfate, coralline hydroxyapatite, Biocoral, tricalcium phosphate, calcium phosphate, PMMA, bone morphogenic proteins, other materials described herein, or combinations thereof.

In certain embodiments, the cement can be radiopaque and can rapidly harden after application. The cement can also have a sufficiently low viscosity to allow injection of the cement through an appropriate cannula to the damage site. One example of bone cement that is suitable for use with certain embodiments disclosed herein is the OsseoFix+ Radiopaque Bone Cement available from Alphatec Spine® Inc.

Figure 18:
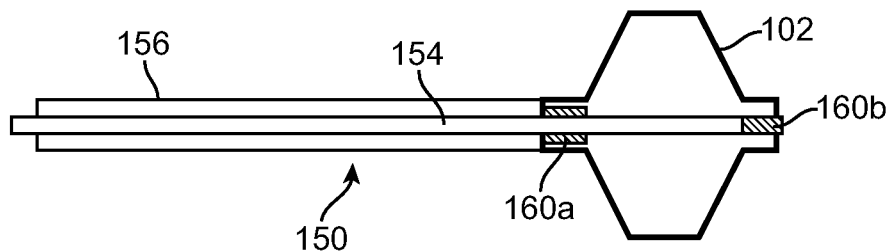
FIGS. 18-20 illustrate a variation of a method for adjusting and/or retracting the expandable support device with an engagement, device.

FIG. 18 illustrates that the deployment tool 150, such as an engagement device, can be configured to attach to the implanted expandable support device to contract the expandable support device 102. This may be necessary to remove or reposition the expandable support device 102. The engagement device can have one or more engagement elements 160, such as first and second engagement elements 160a and 160b. The engagement elements 160 can be on the radial inside and/or radial outside of the engagement device. For example, the engagement elements can be on an inner rod 154 that can be translatably and/or rotationally slidably attached to an outer handle 156. The engagement elements 160 can be a screw thread, a keyed slot, a toggle, ball and socket, an interference fit, a clip, a ratchet, a magnet, glue, an expanding anchor clip, an abutment, a hook, or combinations thereof. The engagement device can be the deployment device (e.g., the deployment tool or other device originally used to deploy the expandable support device 102).

Figure 19:
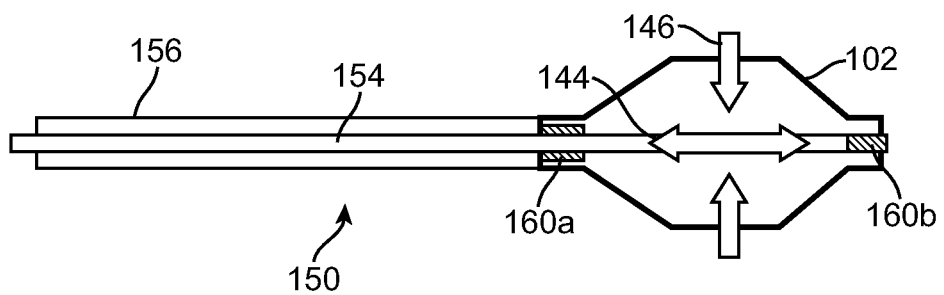

FIG. 19 illustrates that the engagement device 150 can attach to the expandable support device 102. The expandable support device 102 can be configured to releasably attach to the engagement elements 160 at discrete locations (e.g., along discrete lengths of the inner diameter of the expandable support device 102).

The first engagement element 160a can attach to the proximal end 113 of the expandable support device 102. The first engagement element 160a can be an abutment. The second engagement element 160b can attach to the threaded portion 116 at the distal end 114 of the expandable support device 102. The second engagement element 160b can be a threaded outer surface. The expandable support device 102 can have a threaded inner radius 116, for example, that can be configured to engage the threaded outer surface of the second engagement element 160b.

FIG. 19 illustrates that a tensile force, as shown by arrows 144, can be applied to the ends of the expandable support device 102, for example, via the engagement device 105 and the first and second engagement elements 160a and 160b. For example, the inner rod 154 can be pushed distally while the outer handle 156 can be concurrently pulled proximally. The radius of the expandable support device 102 can contract, as shown by arrows 146.

Figure 20:
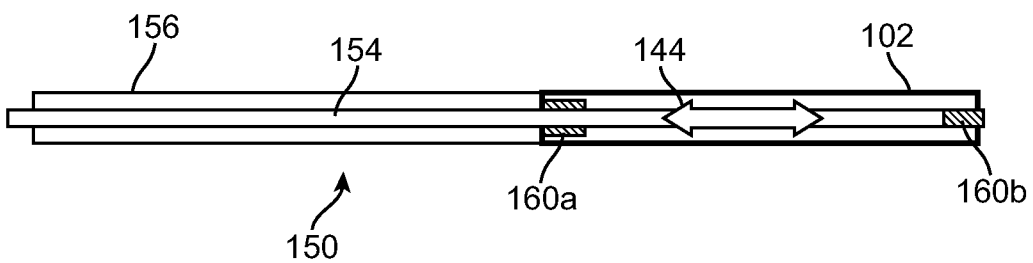

FIG. 20 illustrates that the tensile force, shown by arrows 144, can longitudinally expand the expandable support device. The expandable support device 102 can radially contract, for example, until the expandable support device 102 is in a configuration completely or substantially equivalent to the configuration of the expandable support device 102 before the original deployment of the expandable support device to the treatment site. For example, the expandable support device 102 can have a maximum outer radius that is equal to or smaller than the inner radius of the portion (e.g., the outer handle 156) of the deployment tool 150 into which the expandable support device 102 can be configured to retract.

Examples of methods and devices for deploying expandable support devices are disclosed in U.S. patent application Ser. No. 12/456,602, incorporated herein in its entirety.

The expandable support devices 102 shown above can be surgically inserted into a damaged site by any of the methods disclosed in detail above. In a particular embodiment, the expandable support device 102 is surgically inserted into a vertebral body and fixed in place by using, for example, bone cement in order to repair a compression fracture. An attachable member 103, for example a polyaxial screw or other suitable spinal fixation device, is then attached to the expandable support device 102, as discussed above and further below. The attachable member 103 can then be used to attach/support any number of orthopedic devices.

In one embodiment, after the expandable support device 102 has been deployed, a pedicle screw 103 such as described above can be attached to the proximal end of the expandable support device 102. The deployment tool 150 can be removed by unthreading the distal tip of the deployment rod 154 from the expandable support device 102. A pedicle screw having a threaded end can be delivered over the K-wire (or through the working cannula in some embodiments), aligning the distal end of the polyaxial screw with the proximal end of the deployed implant and threading the polyaxial pedicle screw 103 onto the expandable support device 102 using a suitable screw driving tool (preferably an Allen wrench, not shown). In some embodiments, multiple pedicle screws can be delivered to adjacent vertebra, with fixation rods being secured to the pedicle screws to provide fixation to the adjacent vertebra. Each of these pedicle screws may be attached to an expandable implant in the vertebral body, or alternatively, some of the pedicle screws may be delivered directly into the pedicle bone without use of the expandable implant.

In an alternative embodiment, a hollow pedicle screw 103 and expandable support device 102 can be inserted into the patient simultaneously. In this embodiment, the polyaxial pedicle screw is attached to the expandable support device 102 and then the screw/implant system is attached to an alternative implant inserter (not shown). The polyaxial pedicle screw is preferably attached to the implant via screw threads. However, in some embodiments, the polyaxial pedicle screw can be permanently attached to the implant. The alternative inserter is configured to have a screw driving connection (preferably an Allen wrench type connection) to apply a rotational torque to the polyaxial pedicle screw as the screw/implant is inserted into the vertebra. In some embodiments, the alternative implant inserter can also grip or hold the polyaxial pedicle screw by contacting the polyaxial pedicle screw and/or applying pressure to grip the polyaxial pedicle screw. In other embodiments, the alternative implant inserter can grip or hold the polyaxial pedicle screw via magnetic force. The inserter, with the screw/implant together, may be delivered over a K-wire and/or through a working cannula into a drilled bore of a pedicle into a vertebral body as described above. The inserter can be cannulated to help facilitate this process. The bore preferably has a diameter slightly larger than the unexpanded diameter of the implant, but smaller than the outer threads of the pedicle screw. As the inserter delivers the screw and implant into the bore, the inserter can be rotated to cause the screw threading to engage the pedicle bone.

The pedicle screw of this embodiment preferably has an inner lumen configured to receive an actuator as described above configured to deploy the implant. The inserter may also be hollow and have a similar structure to inserter described above to receive the actuator therein. Once the pedicle screw and implant are advanced to a desired position in the pedicle and vertebral body, the actuator can be rotated to deploy the implant. The actuator can then be removed from the lumen of the pedicle screw and inserter, and bone cement may be delivered through the lumen of the inserter and pedicle screw to the expanded implant. The inserter may then be detached from the pedicle screw and removed from the patient, leaving the pedicle screw and expanded implant.

Imaging methods can be used in combination with the methods for deploying the expandable support device described herein. For example, imaging methods can be used to guide the expandable support device during deployment. The expandable support device 102 can have imaging markers (e.g., echogenic, radiopaque), for example to signal the three-dimensional orientation and location of the expandable support device during use of an imaging modality. Imaging modalities include ultrasound, magnetic resonance imaging (MRI, fMRI), computer tomography (CT scans) and computed axial tomography (CAT scans), radiographs (x-rays), fluoroscopy, diffuse optical tomography, elastography, electrical impedance tomography, optoacoustic imaging, positron emission tomography, and combinations thereof.

FIGS. 21-27 illustrate some examples of orthopedic devices for use with embodiments of the present invention including, but not limited to: the ZODIAC® Spinal Fixation System (FIGS. 21 and 22), the ZODIAC-ROC Lumbar Fixation System (FIG. 23), the DELTALOC® REVEAL Anterior Cervical Plating System (FIG. 24), the SOLANAS® Posterior Cervico-Thoracic Fixation System (FIG. 25), the TRESTLE™ Anterior Cervical Plating System (FIG. 26), anterior lumbar plate (FIG. 26), and the TAMARACK® Anterior Thoracolumbar Plating System (FIG. 27), all of which are available at: http://www.alphatecspine.com/products.asp.

Figure 21:
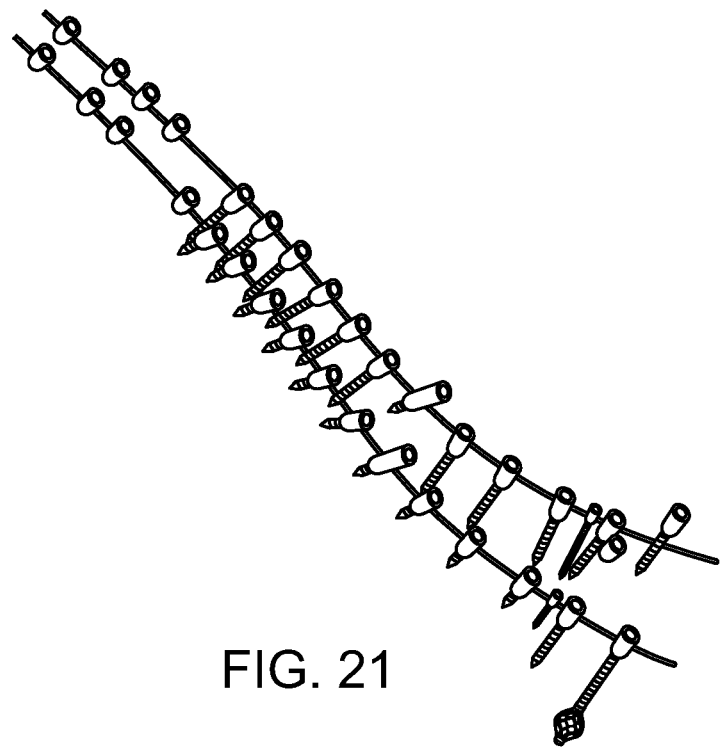
FIGS. 21 through 27 show various embodiments of orthopedic devices that can be used with the expandable support devices and associated attachable members described herein.
Figure 22:
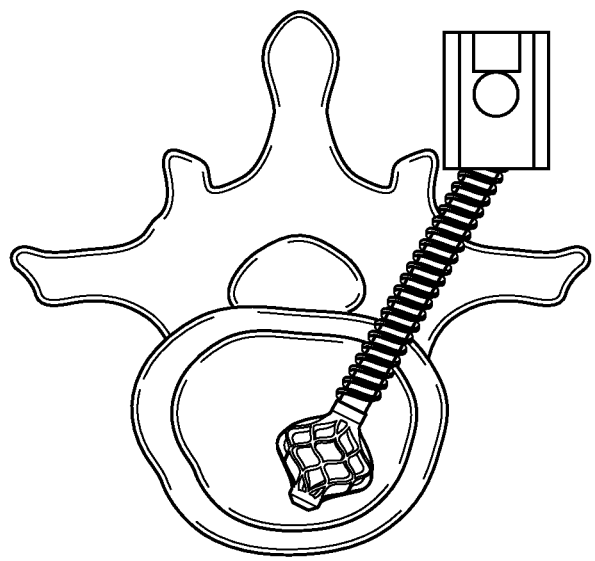

FIG. 21 shows how the ZODIAC® Spinal Fixation System (FIG. 22) is normally attached to the posterior side of a healthy vertebra through the pedicle of the vertebra using a polyaxial pedicle screw with a housing to connect the head of the screw to a rod of the ZODIAC® Spinal Fixation System. However, in other embodiments involving weak/damaged vertebra, one or more of the polyaxial pedicle screws may be replaced with an expandable implant and polyaxial pedicle screw system according to FIGS. 5-20 inserted into the vertebra, as described above, to provide support for the ZODIAC® Spinal Fixation System.

Figure 23:
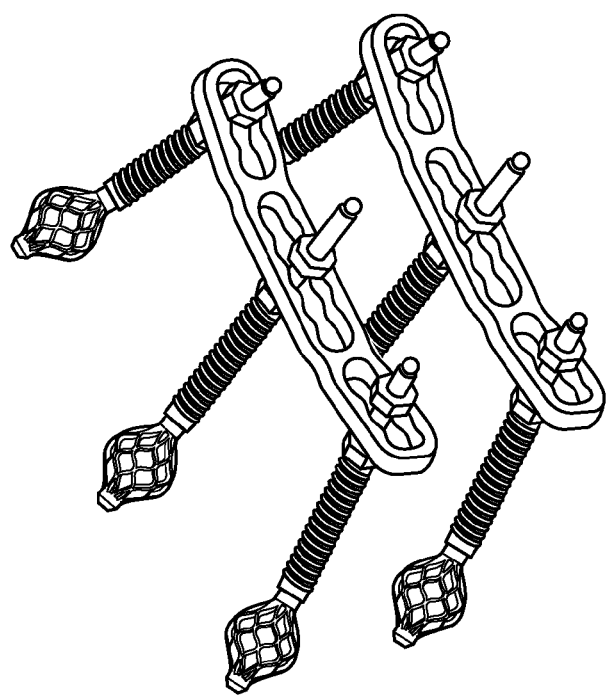

FIG. 23 shows a normal ZODIAC-CORE Lumbar Fixation System which is normally attached with screws to the posterior side of healthy vertebra, typically in the L3-S1 region of the spine. However, in other embodiments involving weak/damaged vertebra, one or more of the ZODIAC-CORE screws may be replaced with the expandable implant and polyaxial pedicle screw system according to FIGS. 5-20 to provide support for the ZODIAC-CORE Lumbar Fixation System.

Figure 24:
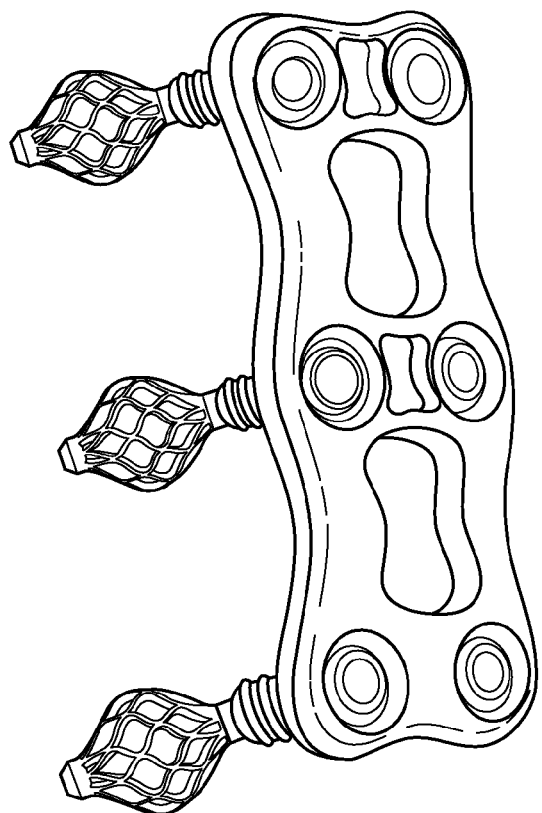

FIG. 24 shows a normal DELTALOC® REVEAL Anterior Cervical Plating System which is normally attached with screws to the anterior side of healthy vertebra using a screw, typically in the C2-C7 region of the spine. However, in other embodiments involving weak/damaged vertebra, one or more of the DELTALOC® REVEAL screws may be replaced with an expandable implant and polyaxial pedicle screw system according to FIGS. 5-20 to provide support for the DELTALOC® REVEAL Anterior Cervical Plating System.

Figure 25:
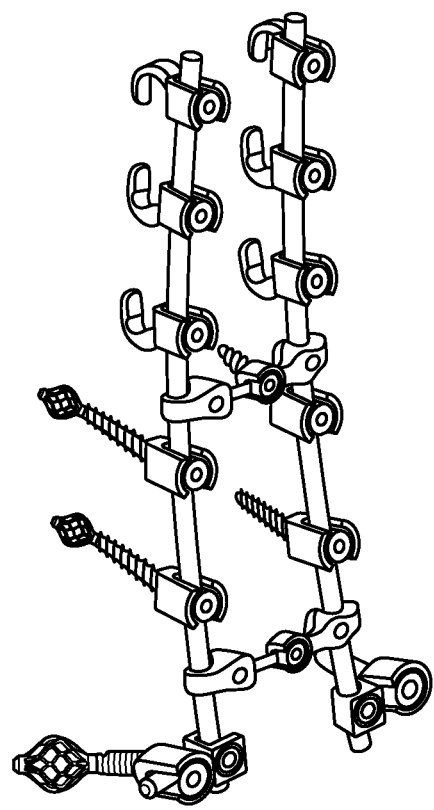

FIG. 25 shows a normal SOLANAS® Posterior Cervico-Thoracic Fixation System which is normally attached with screws to the posterior side of healthy vertebra typically in the T1-T3 region of the spine. However, in other embodiments involving weak/damaged vertebra, one or more of the SOLANAS® screws may be replaced with an expandable implant and polyaxial pedicle screw system according to FIGS. 5-20 to provide support for the SOLANAS® Posterior Cervico-Thoracic Fixation System.

Figure 26:
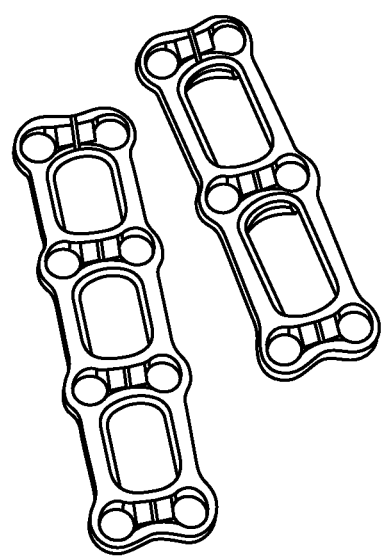

FIG. 26 shows a spinal plate which is normally attached to the anterior side of healthy vertebra typically in the L1-S1 region of the spine with suitable screws (not shown). However, in other embodiments involving weak/damaged vertebra, one or more of the screws may be replaced with an expandable implant and polyaxial pedicle screw system according to FIGS. 5-20 to provide support for the spinal plate.

Figure 27:
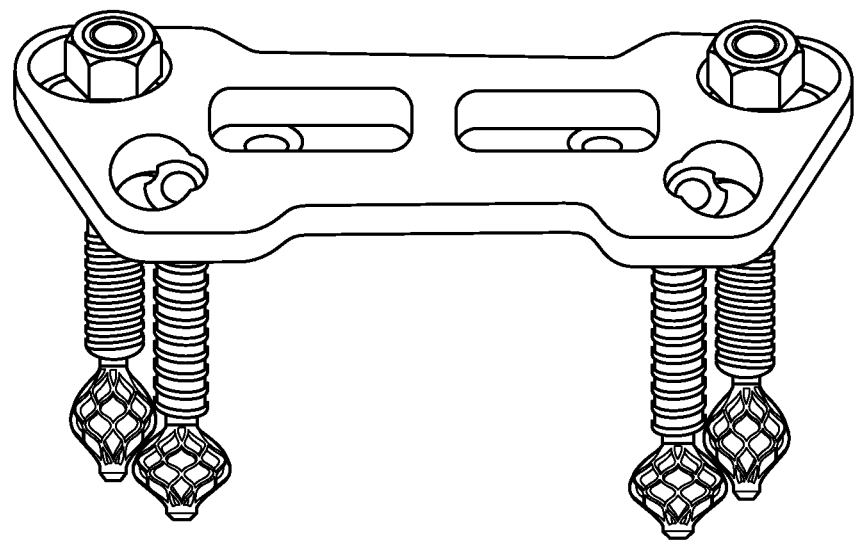

FIG. 27 shows a normal TAMARACK® Anterior Thoracolumbar Plating System which is normally attached to the anterior side of healthy vertebra with screws, typically in the T10-L5 region of the spine. However, in other embodiments involving weak/damaged vertebra, one or more of the screws may be replaced with an expandable implant and polyaxial pedicle screw system according to FIGS. 5-20 to provide support for the TAMARACK® Anterior Thoracolumbar Plating System.

It is apparent to one skilled in the art that various changes and modifications can be made to this disclosure, and equivalents employed, without departing from the spirit and scope of the invention. Elements expressed herein as singular or plural can be used in the alternative (i.e., singular as plural and plural as singular). Elements shown with any embodiment are exemplary for the specific embodiment and can be used in combination on or with other embodiments within this disclosure.

What is claimed is:

1. A system, comprising:
    an expandable support device comprising:
        a body having a proximal end portion, a distal end portion and a longitudinal axis extending there between;
        a plurality of deformable struts located between the proximal and distal end portions, wherein each strut is deformable upon expansion of the expandable support device from an unexpanded condition to an expanded condition, such that the struts deform and the expandable support device expands in the radial direction;
        a deployment tool releasably attached to the proximal end portion and including a deployment rod with a distal tip threadably attached to and fixed relative to the distal end portion and configured to expand or contract the expandable support device through application of compressive or tensile force;
        the expandable support device being configured for delivery within a bony structure; and
    a fixation device releasably attached to the proximal end portion,
    wherein the proximal end portion comprises a threaded portion for releasable attachment of the fixation device.

2. The system of claim 1, wherein the fixation device is a pedicle screw having a threaded end for releasable attachment to the threaded proximal end portion.

3. The system of claim 2, wherein the pedicle screw comprises:
    a head portion, a threaded shaft portion and a tool engagement recess defined by the head portion for use in driving the pedicle screw into bone;
    a body member for receiving said head portion of said pedicle screw therein and defining an opening in an inner end thereof for the extension of said shaft portion of the screw there through, a pair of opposed parallel slots therein for receiving a portion of a fixation rod there between, a curvilinear interior surface disposed about said opening for abutting and mating with said head portion of said screw so as to allow variable angular movement of said body member with respect to said pedicle screw while maintaining said interior surface of said body member in mating contact with said head portion of said screw;
    a locking cap releasably securable within said body member such that said cap bears against the portion of a fixation rod disposed between said slots to secure the rod within said assembly; and
    a keyed interface between said pedicle screw and said body member whereby said pedicle screw can be inserted into a bone and said body member subsequently disposed about said head portion of said screw such that said head portion abuts and mates with said curvilinear interior surface of said body member to provide said variable angular movement of said body member with respect to said screw;
    wherein said keyed interface comprises a first threaded surface in said body member about said opening in said inner end thereof and a second threaded surface on said head portion of said screw, said first threaded surface being adapted to threadably engage said second threaded surface such that said screw can be inserted into a bone and said body member threaded onto and over said head portion of said screw to position said curvilinear interior surface of said body member such that said interior surface can abut and mate with said body portion.

4. The system of claim 2, wherein the deployment tool engages the pedicle screw to apply a compressive force on the expandable support device with the deployment rod.

5. The system of claim 1, wherein the expandable support device is configured to expand into contact with bone within the bony structure.

6. The system of claim 1, wherein the struts can be configured to form a plurality of diamond-shaped ports in the body.

7. The system of claim 1, wherein the struts can be configured to form a plurality of ingrowth ports in the body.

8. The system of claim 1, wherein the fixation device includes a spinal plate system.

9. The system of claim 1, further comprising a threaded element on the proximal end portion of the body that attaches to a threaded element in a distal end portion of the fixation device.

10. A system, comprising:
    two or more expandable support devices, each comprising:
        a body having a proximal end portion, a distal end portion and a longitudinal axis extending there between;
        a plurality of deformable struts located between the proximal and distal end portions, wherein each strut is deformable upon expansion of the expandable support device from an unexpanded condition to an expanded condition, such that the struts deform and the expandable support device expands in the radial direction;
        one or more deployment tools releasably attached to the proximal end portion and including a deployment rod with a distal tip threadably attached to and fixed relative to the distal end portion and configured to expand or contract the expandable support devices through application of compressive or tensile force;
        the expandable support device being configured for delivery within a bony structure; and
    one or more fixation devices releasably attached to the proximal end portions,
    wherein each proximal end portion comprises a threaded portion for releasable attachment of the fixation device.

11. The system of claim 10, further comprising at least one fixation rod coupled to the one or more fixation devices.

12. The system of claim 10, further comprising at least one spinal plate coupled to the one or more fixation devices.

13. The system of claim 10, wherein the fixation device is a pedicle screw comprises:
- a head portion, a threaded shaft portion and a tool engagement recess defined by the head portion for use in driving the pedicle screw into bone;
- a body member for receiving said head portion of said pedicle screw therein and defining an opening in an inner end thereof for the extension of said shaft portion of the screw there through, a pair of opposed parallel slots therein for receiving a portion of a fixation rod there between, a curvilinear interior surface disposed about said opening for abutting and mating with said head portion of said screw so as to allow variable angular movement of said body member with respect to said pedicle screw while maintaining said interior surface of said body member in mating contact with said head portion of said screw;
- a locking cap releasably securable within said body member such that said cap bears against the portion of a fixation rod disposed between said slots to secure the rod within said assembly; and a keyed interface between said pedicle screw and said body member whereby said pedicle screw can be inserted into a bone and said body member subsequently disposed about said head portion of said screw such that said head portion abuts and mates with said curvilinear interior surface of said body member to provide said variable angular movement of said body member with respect to said screw;
- wherein said keyed interface comprises a first threaded surface in said body member about said opening in said inner end thereof and a second threaded surface on said head portion of said screw, said first threaded surface being adapted to threadably engage said second threaded surface such that said screw can be inserted into a bone and said body member threaded onto and over said head portion of said screw to position said curvilinear interior surface of said body member such that said interior surface can abut and mate with said body portion.

* * * * *